United States Patent [19]

Sedlacek et al.

[11] 4,166,106

[45] Aug. 28, 1979

[54] IMMUNOLOGIC DETERMINATION METHOD

[75] Inventors: Hans-Harald Sedlacek; Roloff Johannsen; Friedrich-Robert Seiler, all of Marburg, Fed. Rep. of Germany

[73] Assignee: Behringwerke Aktiengesellschaft, Marburg, Fed. Rep. of Germany

[21] Appl. No.: 835,789

[22] Filed: Sep. 22, 1977

[30] Foreign Application Priority Data

Sep. 25, 1976 [DE] Fed. Rep. of Germany ....... 2643208

[51] Int. Cl.$^2$ ............................................. G01N 33/16
[52] U.S. Cl. .................................... 424/12; 23/230 B; 435/7; 424/1; 424/8

[58] Field of Search ....................... 23/230 B; 424/12; 195/103.5 A

[56] References Cited

PUBLICATIONS

E. A. Kabat, "Structural Concepts in Immunology and Immunochemistry," 162–168, Holt, Rinehart and Winston, Inc., New York, 1968.

Primary Examiner—Sidney Marantz
Attorney, Agent, or Firm—Curtis, Morris & Safford

[57] ABSTRACT

A method for determininng a reagent capable of immunologic reaction by direct or indirect test methods, wherein an antigen is contacted with the Fc fragment of an immune globulin prior to contacting it with an antibody having no specificity to said Fc fragment, whereby unspecific linkages arre decreased.

6 Claims, No Drawings

IMMUNOLOGIC DETERMINATION METHOD

The present invention relates to an improved process for the qualitative or quantitative determination of a reactant of an immunologic reaction, utilizing the known affinity of antibodies and antigens to each other, by decreasing unspecific linkages. The invention is based on the fact that such reactions can be recorded more distinctly by means of certain identification criteria.

In principle, there are two different kinds of immunologic reaction methods with marked reactants: the direct test and the indirect techniques.

For the direct test, the reactant to be determined, in most cases an antigen is determined by incubation with a marked second reactant specifically directed against the antigen, generally an antibody.

For the indirect techniques, the reactant to be determined is incubated with a second reactant specifically directed against it and, after separation and elimination of the unbound amount of the second reactant, the reaction mixture is incubated with a third, generally marked, reactant specifically directed against the second one.

It is known to those skilled in the art that the direct test is distinguished by a high specificity. However, its disadvantage resides in an insufficient sensitivity. On the other hand, the indirect techniques are known for their high sensitivity but low specificity.

One of the essential factors influencing the specificity in the direct and indirect tests is supposed to be the unspecific linkage of the antibodies to the antigen and the structures surrounding it.

An unspecific linkage is mainly caused by sections of the so-called Fc part of the antibody (=immune globulin) molecule, and this goes also for highly specified antibodies.

The binding affinity of the Fc parts of an antibody to various structures of cells or tissues described in the literature as Fc receptors is increased when a change of conformation occurs in the antibody molecule. This change takes place on the occasion of spontaneous aggregation of antibody molecules in antibody preparations, linkage of antibodies to an antigen (immune complexes), or adsorption of antibody molecules onto synthetic surfaces, for example latex particles.

Hitherto, various methods for decreasing the unspecific linkage have been applied, for example elimination of aggregates or immune complexes from antibody preparations by means of ultracentrifugation, addition of albumin to the antibody preparations in order to stabilize the proteins or to prevent aggregate formation.

Additionally, in the direct and indirect tests there have been used with success such antibody preparations the Fc part of which had been split off according to known methods without adversely affecting the immunologic reaction of the remaining fragment $F(ab)_1$ or $F(ab)_2$. These methods, however, because $F(ab)_1$ or $F(ab)_2$ fragments of the antibodies have to be specially obtained, are complicated and expensive. Moreover, the corresponding operations are very difficult to carry out in some cases, especially when antisera are used in the indirect tests.

In accordance with the present invention, the direct and indirect tests for the immuno-reaction with marked reactants are altered in a simple manner and to such an extent that the known high sensitivity is completely maintained also in the case where natural antibodies or sera containing such antibodies are used, while the known high unspecificity is reduced to a minimum.

The present invention is based on the idea that in the direct and indirect tests the unspecific linkage of natural antibodies due to Fc can be prevented when the structures of various antigens which react with the Fc part (in a general sense Fc receptors) are previously saturated by immune globulin fragments having a binding affinity to these Fc receptors in a general sense. Such immune globulin fragments should stem from immune globulins of that species from which either the antibody (direct test) or the first antibody (indirect techniques) is derived. On the other hand, all antibodies used must not have any specificity to this immune globulin fragment. Furthermore, as far as this is required according to the test, the immune globulin fragments must not fix a complement.

A possible steric hindrance of the specifically immunologic reaction, such as occurs for example when using natural immune globulins or immune globulin aggregates instead of immune globulin fragments, is not observed when immune globulin fragments having an affinity to Fc receptors are employed.

Furthermore, the application of immune globulin fragments, for example Fc fragments of different immune globulin classes, allows the use of antibodies directed against parts of immune globulins, for example the light chains thereof, the Fd fragment or F(ab) fragments of the corresponding immune globulin classes, in the direct and indirect tests without the risk of an immunologic reaction with the Fc fragment.

The present invention relates to a process for the qualitative or quantitative determination of a reactant of an immunologic reaction according to the direct test or the indirect techniques, which comprises contacting an antigen bearing Fc receptors in a general sense with an immune globulin fragment having a binding affinity to Fc receptors in a general sense, and subsequently bringing it into contact with antibodies having no specificity to the immune globulin fragment. Thus, a considerable improvement in the result of an immunologic determination is achieved by decreasing unspecific side reactions.

By indirect techniques in accordance with this invention, there are to be understood all tests in which the intended reactant is detected by more than one further reactant only. Therefore, indirect techniques in accordance with this invention are especially the antiglobulin test, the direct test with complement, and the sandwich test.

These methods are described in detail in J. H. Humphrey, R. G. White, Kurzes Lehrbuch der Immunologie, Stuttgart 1975, pp 257–260; D. M. Weir, Handbook of Experimental Immunology, Oxford 1973, pp. 18.14–18.16; and G. Wick, Wiener klinische Wochenschrift (1972), 84.1, pp 2–7, using fluorescent dyestuffs as identification criteria.

The methodology of the indirect techniques can be extended in such a manner that all antibodies used are marked and/or that, in addition to a third reactant, further reactants specifically directed against the preceding reactant may be employed.

Therefore, all those processes according to which incubation with marked antibodies is carried out several times are indirect techniques, too.

It is known from the literature that certain sections of the Fc part of immune globulin have a high affinity to Fc receptors in a general sense. It is furthermore known that antibody molecules (immune globulin molecules) are disintegrated by means of proteolytic enzymes to form numerous fragments. Thus, the proteinases plasmin or papain divide the immune globulin molecule into two $F(ab)_1$ fragments and one Fc fragment. Pepsin attacks the molecule at another place and causes the formation of a bivalent so-called $F(ab)_2$ fragment and further little peptides, for example pFc. These proteolytic degradation products of the antibody molecule denominated Fc fragments or pFc can be used in accordance with this invention as immune globulin fragments having an affinity to Fc receptors in a general sense.

Examples of preparation of Fc fragment or pFc are described in Porter, R. P. (1959), Biochem. J. 73, 119; Hershgold, E. J. et al. (1963) Nature 199, 284; and Haupt; H. (1969), Klin Wschr. 47, 270.

The methodology of the direct test and the indirect techniques may be succinctly described and exemplified as follows:

In the direct test, the antigen containing substrate is contatacted with a marked reactant, generally a specific antibody, which causes the antibody to be linked to the corresponding antigen. Thus, the antigen is identified directly.

According to the indirect techniques, the intended reactant (for example the antigen) is detected by more than one further reactant.

In the antiglobulin test, for example, the antigen containing substrate is reacted with a specific antibody which is optionally marked, the excess antibody is eliminated from the reaction mixture by washing, and the reaction mixture is reacted with a second marked antibody specifically directed against the first antibody, and subsequently the amount of unbound antibody is removed.

In the sandwich test, an antibody is reacted with the antigen specifically directed against it, the unbound amount of the antigen is eliminated, and the reaction mixture is reacted with a marked antibody again specifically directed against the antigen, and the unbound amount of the antibody is removed.

In the indirected test with complement, the antigen substrate either fixes complement directly, or it is reacted with a complement-fixing antibody specifically directed against the antigen; subsequently, unbound antibody is removed, and the reaction mixture is reacted with complement. After elimination of the unfixed complement amount, the complement fixed to the antigen or antigen/antibody complex is detected by means of a marked antibody specifically directed against complement.

Within the scope of this invention the expert is of course free to use those identification media known to him, for example marking with fluorescent dyestuffs, radioactive marking or enzyme marking.

The use of immune globulin fragments having an affinity to Fc receptors in a general sense according to this invention may be succinctly exemplified and described as follows for the direct test as well as for the antiglobulin test.

For the detection or determination of an antigen in accordance with this invention, the sample to be tested or a dilution series thereof is contacted with different amounts, beginning for example with 1 mg, of an immune globulin fragment which has a binding affinity to Fc receptors in a general sense, for example the Fc fragment of IgG after fission by papain. Subsequently, the mixture is allowed to stand for a period of from 20 minutes to 20 hours, preferably for about 30 minutes, at a temperature of from 4° to 30° C., preferably about 20° C., in a water vapor-saturated atmosphere.

Thereafter, unbound Fc fragment is separated from the reaction mixture, for example by repeated washing (generally twice), preferably with a polyionic, isotonic aqueous solution. Subsequently, the reaction mixture is contacted with a determined amount of the marked antibody specifically directed against the antigen (direct test) or an antiserum or an unmarked antibody (antiglobulin test), and the mixture is then allowed to stand for 20 minutes to 20 hours, preferably about 30 minutes, at a temperature of from 4° to 30° C. in a water vapor-saturated atmosphere.

Unbound antibodies are removed from the reaction mixture by repeated washing of the latter (generally to 2 to 6 times), preferably with a polyionic, isotonic aqueous solution. Subsequently, in the case of the antiglobulin test, the reaction mixture is contacted with a determined amount of a marked antibody specifically directed against the first antibody, and then incubated and washed under the conditions as described for the antibody used first.

Thereafter, depending on the kind of antigen used, the reaction mixture is spread onto a slide (for example cell suspension) or it is already fixed to a carrier (histological section).

Examination is then carried out using apparatus for qualitative and quantitative measurement and observation known to those skilled in the art and marketed by corresponding specialized companies, such as fluorescence microscopes with direct light or transmitted light excitation, fluorescence photometers or radiation measuring devices.

The optimum amount of immune globulin fragment having a binding affinity to Fc receptors, for example of the Fc fragment, in order to prevent unspecific linkage can be easily evaluated by a preliminary test for any specific antigen.

Suitable antigens are for example viral antigens (for example rubella, measles or hepatitis antigens), bacterial antigens (for example Salmonella, Escherichia coli or staphylococci antigens), carbohydrate antigens (for example blood group substances), protein antigens (for example plasmoproteins such as immune globulins or complement factors), glycoprotein antigens (for example $\alpha_1$-antitrypsin, caeruloplasmin), or lipoprotein antigens (for example $\alpha_1$-lipoprotein). They may be isolated, dissolved, suspended, linked to carriers such as water-insoluble polymers, for example chemically cross-linked carbohydrates, be present in or on cells, or in histological tissue sections.

The immune globulin fragments required for obtaining immune globulin fragments having a binding affinity to Fc receptors in a general sense are prepared in known manner from the blood or serum of man or animal; however, synthetic immune globulin fragments may also be used within the scope of this invention.

The decrease of unspecific linkage of specific antibodies, although their sensitivity in the direct and indirect tests remains unchanged, which decrease is achieved in accordance with this invention by using immune globulin fragments having a binding affinity to Fc receptors, for example Fc fragments, is proved by the following tests, the results of which are partially listed in the following Tables:

Table 1 shows results proving the influence of Fc fragments of human IgG on the unspecific linkage of rabbit gamma globulin to the surface of lymphocytes of two donors (columns A and B), and the dependence thereof on a preliminary incubation of the lymphocytes with neuraminidase (columns C and D). As already described (Seiler et al. (1974) Behring Inst. Mitt. 55, 258), a neuraminidase treatment of lymphocytes increases the amount of cells bearing Fc receptors.

Table 1 (columns B and D) shows that the unspecific linkage of rabbit gamma-globulin to lymphocytes according to the double antibody method is substantially reduced by a preliminary treatment with Fc fragments, as compared to cells not treated with Fc fragments (columns A and C).

When in a further example frozen sections of different organs, for example liver or kidney of mouse, rat, rabbit or man, are spread onto glass slides according to known methods, subsequently incubated for 30 minutes in a moisture chamber at 20° C. with about 0.1 ml of a 1% or 0.1% solution of Fc fragments of human IgG, then washed gently in isotonic saline solution, and when thereupon a double antibody test is carried out in known manner (indirect method: G. Wick (1972) Wein.-klin. Wschr. 84, 2-7) with the use of human antisera as first antibody and a second antibody not cross-reacting with the Fc fragment, there results a lower rate of unspecific linkage of the antibodies to the frozen section than in the case of a frozen section not treated with Fc fragments as described above.

TABLE 1:

Inhibition of unspecific linkage of normal rabbit gamma globulin to human peripheric lymphocytes by Fc fragments of human IgG in the indirect method

|  | | A | | B | | | C | D | |
|---|---|---|---|---|---|---|---|---|---|
| | VCN | − | − | − | − | + | + | + | + |
| | Fc | − | 1+ | 10 | 100 | − | 1 | 10 | 100 |
| Donor I | | | | | | | | | |
| rabbit | 1+ | 8++ | 3 | 1 | 1 | 55 | 5 | 2 | 5 |
| γ-globulin | 4 | 6 | 4 | 2 | 1 | 34 | 4 | 2 | 3 |
| donor II | | | | | | | | | |
| rabbit | 1+ | 11 | 2 | 3 | 3 | 12 | 4 | 5 | 5 |
| γ-globulin | 4 | 5 | 2 | 6 | 1 | 17 | 14 | 3 | 17 |
| | | 16 | 4 | 6 | 2 | 8 | 9 | 12 | 10 | 7 |

VCN = Vibrio cholerae neuraminidase 25 U/5 × 10⁷ cells, 30 min. 37° C.
Fc = Fc-fragment of human IgG, 1% stock solution. 0.1 ml of each dilution on 5 × 10⁶ cells (sediment) for 30 min. at room temperature, subsequently 2 washings.
+ = reciprocal titer of the antibody or Fc dilution
++ = unspecifically dyed lymphocytes in %.

The example of following Table 2 proves that saturation of Fc receptors on lymphocytes, for example by means of Fc fragments, does not result in a steric hindrance of adjacent antigen structures, in contrast to the use of immune globulin aggregates.

In this Example, lymphoblastoid culture cells of B type lymphocytes/RPMI 1788) were incubated with an antiserum (serum 196602), which hinders the so-called mixed lymphocyte culture (MLC). Because of the congruence of antigen structures of B type lymphocytes in the MLC and the lymphoblastoid culture cell, antibodies of this antiserum are linked to the lymphoblastoid cell. These antibodies can be detected by a marked second antibody directed against the first one (FITC anti-IgM or FITC anti-k+anti-l). It is known that unspecific reactions of the Fc part of the immune aggregates or immune complexes present in the antibody preparations give falsely positive results. A preliminary saturation of the so-called Fc receptors on the cells by means of aggregates of immune globulin G makes it impossible for practically all antibodies to be linked to the cell, (see column C and the corresponding literature) possibly because of steric hindrance. When Fc fragments are used instead of immune globulin aggregates, such inhibition of the antibodies does not occur (column D), although Fc fragments saturate the Fc receptors, which is proved by the fact that subsequently used immune globulin aggregates are not linked to the cell any more (column E).

On account of these observations, the process of the invention is therefore especially suitable for improving an immunologic reaction by decreasing unspecific linkage in the determination processes of cytoplasmic or cell membrane antigens (especially MLC determinants), or of nucleus antigens, antigens in the tissue or on carriers, or antibodies which are dissolved.

TABLE 2:

Inhibition of linkage of aggregated IgG by Fc fragments of IgG.
Target cell: RPMI 1788

| Column | Fc | IgG aggr. | Serum 196602 | FITC Anti-IgM | FITC Anti-k + Anti-l |
|---|---|---|---|---|---|
| A | − | − | − | 18+ | 22+ |
| B | − | − | + | 28 | 40 |
| C | −+ | + | 0 | 0 | |
| D | + | − | + | 35 | 43 |
| E | + | + | + | 31 | 40 |

+ % dyed lymphoblasts

The following example of detection of cell membrane-linked MLC determinants on lymphocytes illustrates the invention.

EXAMPLE

According to known methods, human peripheric lymphocytes are isolated from venous whole blood. The lymphocyte suspension so obtained is a cell mixture consisting substantially of B type and T type lymphocytes. The T type cells are separated as far as possible according to known methods, and rejected. The remaining lymphocytes enriched with B type cells are washed twice in an isotonic saline solution. A number of cell sediments, 1×10⁶ lymphocytes each, are resuspended each in 0.1 ml of a 1% solution of Fc fragment of IgG (this rate has proved to be the optimum according to preliminary tests) and incubated for 30 minutes at room temperature. The batches are then washed twice with isotonic saline solution. Each batch (cell sediment) is resuspended in 0.1 ml of a human serum to be tested and incubated at room temperature. In this Example, 9 test sera and one negative control serum (AB) are used. Subsequently, the reaction mixture is washed 3 times with an isotonic saline solution.

The sediment is resuspended in 0.05 ml of a fluorescin marked rabbit antibody directed against the light chains of human immune globulins (1% protein solution), incubated for 30 minutes at room temperature, and subsequently washed 3 times with an isotonic saline solution.

Subsequently, the sediment is resuspended in 0.05 ml of bovine serum albumin solution (2% w/v), the suspension is spread onto a slide, air-dried and embedded in glycerol according to known methods.

By means of a fluorescence microscope, the amount of fluorescing cells in the totality of cells is counted and indicated in percent.

Result: The number of positive cells after treatment with Fc fragment is indicated in column II of the following Table 3. It is evident that, as compared to the values obtained with the same antibodies but without treatment with Fc fragment (column I), there is a decrease of positive cells, which decrease differs depending on the serum used. Thus, differentiation between positive and negative sera is improved.

TABLE 3:

Reduction of unspecific linkage of antigens to lymphocytes by preliminary Fc fragment incubation

| Sera | without Fc | with Fc |
|---|---|---|
| 20075 | 23+ | 12 |
| 20138 | 19 | 14 |
| 20330 | 26 | 11 |
| 10376 | 20 | 10 |
| 20377 | 18 | 17 |
| 20379 | 23 | 9 |
| 20380 | 27 | 12 |
| 20381 | 17 | 10 |
| 20630 | 13 | 11 |
| AB | 11 | 6 |

+% of positive lymphocytes

What is claimed is:

1. In a method for determining a reagent capable of immunologic reaction, which method includes an affinity reaction between an antigen and an antibody, the improvement wherein said antigen is contacted with the Fc fragment of an immune globulin prior to contacting it with said antibody, and said antibody has no specificity to said Fc fragment.

2. A method as in claim 1 wherein an amount of Fc fragment equivalent to the amount of Fc receptors on said antigen is used.

3. A method as in claim 1 wherein said Fc fragment is obtained by enzymatic cleavage of an immune globulin with papain, plasmin, or pepsin.

4. A method as in claim 1, wherein an antibody in solution is determined.

5. A method as in claim 1 wherein an antigen present in cytoplasm, in a cell membrane, in a cell nucleus, or in a tissue is determined.

6. A method as in claim 5 wherein an antigen in mixed lymphocyte culture determinants is determined.

* * * * *